(12) United States Patent
Williams et al.

(10) Patent No.: US 7,784,346 B2
(45) Date of Patent: Aug. 31, 2010

(54) MICROMACHINES ACOUSTIC SENSOR FOR MONITORING ELECTROCHEMICAL DEPOSITION

(75) Inventors: Frances R. Williams, Norfolk, VA (US); Gary S. May, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 1205 days.

(21) Appl. No.: 11/199,102

(22) Filed: Aug. 8, 2005

(65) Prior Publication Data
US 2006/0042388 A1 Mar. 2, 2006

(51) Int. Cl.
*G01N 29/024* (2006.01)
(52) U.S. Cl. ............... 73/597; 73/598; 73/632
(58) Field of Classification Search .......... 73/597, 73/598, 632
See application file for complete search history.

(56) References Cited

U.S. PATENT DOCUMENTS

| | | | | |
|---|---|---|---|---|
| 4,445,384 A | * | 5/1984 | Royer | 73/724 |
| 4,531,267 A | * | 7/1985 | Royer | 29/25.35 |
| 4,783,821 A | * | 11/1988 | Muller et al. | 381/173 |
| 5,230,921 A | * | 7/1993 | Waltonen et al. | 427/100 |
| 5,633,552 A | * | 5/1997 | Lee et al. | 310/311 |
| 7,082,834 B2 | * | 8/2006 | Petrova et al. | 73/708 |
| 7,197,911 B1 | * | 4/2007 | Lilienfeld | 73/28.01 |
| 2002/0152803 A1 | * | 10/2002 | Larson et al. | 73/64.53 |

OTHER PUBLICATIONS

Silicon nitride definition, downloaded Jun. 5, 2008 from en.wikipedia.org/wiki/Silicon_nitride, pp. 1-2.*
J. Franz and D. Hohm. "Silicon Acoustic Sensors." Eurocon '86: Part 2 (1986): 156-161.

* cited by examiner

*Primary Examiner*—Hezron Williams
*Assistant Examiner*—Rose M Miller
(74) *Attorney, Agent, or Firm*—Ryan A. Schneider, Esq.; Troutman Sanders LLP

(57) ABSTRACT

Disclosed are micromachined acoustic sensors for monitoring electrochemical deposition, methods for fabricating such sensors, and methods for in-situ monitoring of electrochemical deposition processes using such sensors. An exemplary acoustic sensor includes a deformable silicon membrane, an encapsulated piezoelectric layer formed on the silicon membrane, and surface electrodes formed on the piezoelectric layer. The sensor and a loudspeaker may be used to calibrate an electrochemical deposition process. The acoustic response of the sensor is monitored over time with respect to plating thickness during electroplating of a sample to generate a predictive model defining the plating process. The predictive model may be used to monitor the plating thickness of other samples in real time.

8 Claims, 2 Drawing Sheets

MICROMACHINES ACOUSTIC SENSOR FOR MONITORING ELECTROCHEMICAL DEPOSITION

GOVERNMENT RIGHTS

The U.S. Government may have a paid-up license in this invention and the right in limited circumstances to require the patent owner to license others on reasonable terms as provided for by the terms of Grant No. EEC-9402723 awarded by the National Science Foundation of the U.S.

BACKGROUND

The present invention relates generally to sensors and fabrication methods, and more particularly, to micromachined acoustic sensors for monitoring electrochemical deposition, methods for fabricating micromachined acoustic sensors, and methods for in-situ monitoring of electrochemical deposition processes using such sensors.

As microsystem feature sizes continue to shrink, the level of integration and complexity of microelectronic devices continues to increase. Microsystems packaging must also evolve to accommodate these trends in integrated circuit (IC) technology. Packaging requirements, such as cost, power, input/output (I/O) count, and operating frequency, for example, must be consistent with IC roadmap projections. Moreover, manufacturing challenges also increase as feature sizes decrease. Improvements in fabrication methods and processes are critical if inexpensive and reliable devices with such small dimensions are to be produced. Semiconductor manufacturing processes require hundreds of successive processing steps, and each of these can potentially contribute to yield loss and increased cost. Therefore, manufacturing technology development requires not only advancement in fabrication processes, but also advances in process monitoring and control.

Effective process control can be provided by in-situ monitoring, process modeling, and real-time, closed-looped operation. In-situ monitoring employs sensors to measure and monitor critical manufacturing process parameters in real time, thus permitting early detection of defective components and process shifts. There is a shortage of sensors that have been developed as in-situ process monitors, however. Many current methods utilize optical techniques to monitor various process parameters. These methods rely on "looking" at a process to monitor its status. While these methods are relatively common for in-situ process monitoring, the equipment they employ can be expensive and can have equipment mounting and calibration challenges.

It would be desirable to have inexpensive and reliable sensors for monitoring electrochemical deposition, methods of fabricating such sensors and methods for in-situ monitoring of electrochemical deposition processes using such sensors.

BRIEF DESCRIPTION OF THE DRAWINGS

The various features and advantages of the present invention may be more readily understood with reference to the following detailed description taken in conjunction with the accompanying drawings, wherein like reference numerals designate like structural elements, and in which.

DETAILED DESCRIPTION

Disclosed below are alternative or complementary techniques to those discussed in the Background section that are based on acoustic methods of in-situ monitoring. Essentially, acoustic methods involve "listening" to the manufacturing process to enhance the amount and sensitivity of data collection to facilitate process diagnostics and control.

Described herein are acoustic devices (microsensors) that function as microphones. The sensing elements of these microsensors are usually bendable beams or membranes of silicon dioxide, silicon nitride, or silicon layers. Because of the application of IC and micromachining fabrication techniques, these elements can be created with a thickness as small as 1-30 µm. See, for example, J. Franz and D. Hohm. "Silicon Acoustic Sensors." Eurocon '86: Part 2 (1986): 156-161. Thus, vibrations from undesired sources are less likely to interfere with the input signal to the microsensors. Also, by using microfabrication techniques, various electrode patterns can be obtained, improving the sensitivity and frequency response of these microsensors.

Disclosed herein is a micromachined piezoelectric microphone sensor 10, or acoustic sensor 10, (FIG. 1e) which may be used for in-situ monitoring of electrochemical deposition processes, such as nickel-iron (Ni—Fe) electrochemical deposition, for example. During operation, changes occur in a plating bath 31 (FIG. 2) used in the electrochemical deposition process as the nickel-iron alloy is deposited. Changes in the process medium (i.e., the solution 32) affect the acoustic response of the acoustic sensor 10. An exemplary acoustic sensor 10 was used in an electroplating process and its response was monitored during depositions. By mapping (calibrating) the response of the acoustic sensor 10 to the corresponding film thickness of the plated alloy measured at certain times, a predictive model of the thickness of the plated alloy was derived as a function of sensor output and plating time. Such a model provides for real-time monitoring of the thickness of the plated nickel-iron alloy, for example. This is discussed in detail below.

Sensor Design and Fabrication

The microphone sensor 10 described herein exploits the piezoelectric effect, in which a mechanical stress applied to a polarized crystal produces a mechanical deformation in the crystal and results in an electric charge.

Figure 1A:
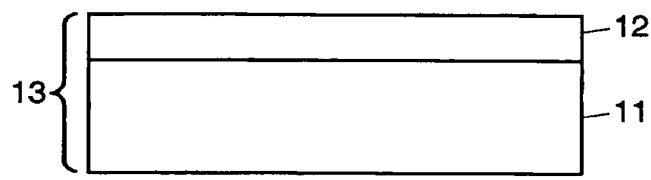
FIGS. 1a-1e illustrate an exemplary fabrication process for making an exemplary micromachined acoustic sensor.
Figure 1B:
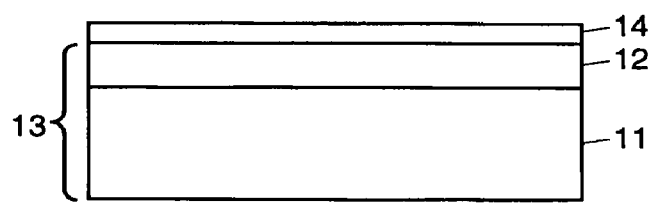
Figure 1C:
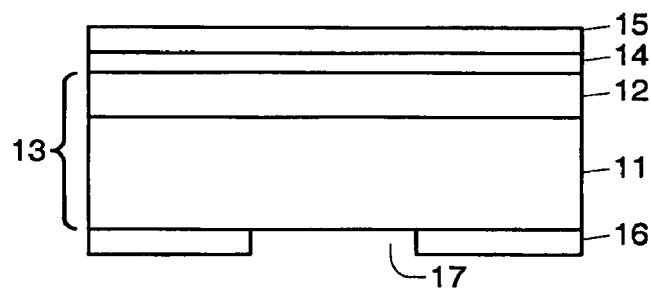
Figure 1D:
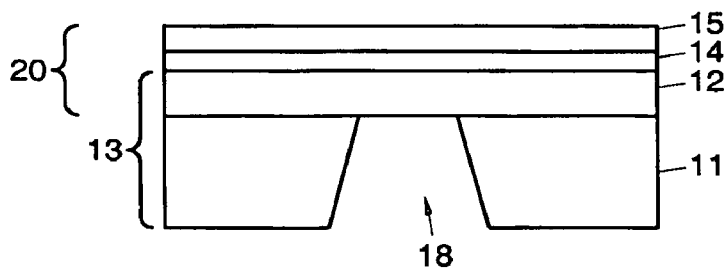
Figure 1E:
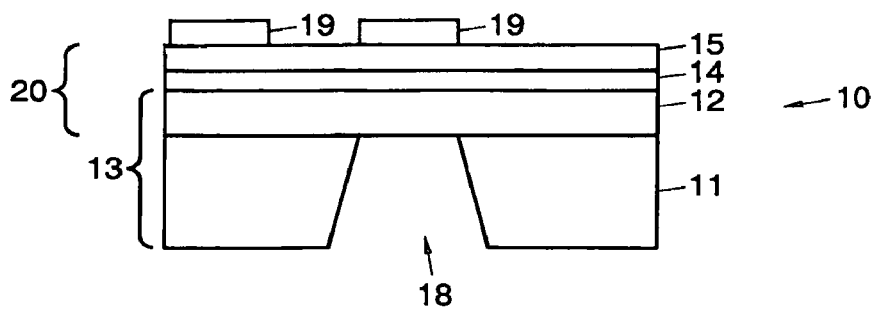

An exemplary reduced-to-practice acoustic sensor 10 is shown in FIG. 1e, and comprises a membrane 12, an encapsulated piezoelectric layer 14, and segmented surface electrodes 19. This concept is generally discussed in J. Franz and D. Hohm. "Silicon Acoustic Sensors." Eurocon '86: Part 2 (1986): 156-161. A highly doped silicon layer comprises the membrane 12 because silicon does not possess the tensile stress associated with silicon nitride or silicon dioxide layers. An exemplary silicon membrane 12 is approximately 3.5 µm thick. Zinc oxide (ZnO) serves as the piezoelectric layer 14 and is approximately 0.8 µm thick. The ZnO piezoelectric layer 14 is encapsulated by a silicon nitride layer 15, which helps to reduce surface charge leaks. An exemplary deflectable diaphragm structure 20, or diaphragm 20, comprising the membrane 12, piezoelectric layer 14, and silicon nitride layer 15, and which is the sensing element of the microphone sensor 10, has dimensions of 1270 µm×1270 µm.

To optimize performance, the microphone sensor 10 was modeled using finite element analysis software. The results of the analysis indicated that movement of the sensor's membrane 12 due to sound pressure experiences the greatest bending stress in the middle and outer region of the defined area of the diaphragm 20. Thus, electrodes 19 (FIG. 1e) were placed in these regions on a surface of the sensor 10.

Referring to FIGS. 1a-1e, they illustrate an exemplary fabrication process 20 for making a micromachined acoustic sensor 10. The sensor 10 was fabricated using IC and micromachining techniques, enabling the batch fabrication of small, precise devices that may be reproduced. A two-inch n-type (100) silicon wafer 13 (substrate 13 or layer 13) was doped with a high concentration of boron atoms to form a doped silicon layer 12 at the top surface (FIG. 1a). The doped silicon layer 12 comprises the membrane 12. The doped silicon layer 12 acted as an etch stop in a later processing step. A thin piezoelectric layer 14 comprising ZnO was then deposited by RF sputtering (FIG. 1b). Silicon nitride layers 15, 16 were deposited over the ZnO piezoelectric layer 14 as well as on the back of the wafer 11 using plasma-enhanced chemical vapor deposition (FIG. 1c). The silicon nitride layer 15 forms an encapsulating layer over the piezoelectric layer 14. The silicon nitride layer 16 on the back side of the silicon wafer 13 comprises a masking layer 16.

A post-deposition anneal in an inert gas was performed to relax the stress in the ZnO piezoelectric layer 14. The silicon nitride layer 16 on the back side of the wafer 11 was patterned to define an opening 17 in the silicon nitride layer 16 (FIG. 1c). The pattern, which defined the surface of the diaphragm 20 was etched into the silicon nitride layer 16 by reactive ion etching (FIG. 1c). The wafer 13 was then back-etched in an aqueous solution of potassium hydroxide (KOH) to produce an opening 18 on the back side of the silicon wafer 11. The boron-doped silicon layer 12 of the silicon wafer 13, as well as the slower etching (111) planes of the silicon wafer 13, were used as an etch stop to produce the opening 18. The (111) planes the silicon wafer 11 delineated a relatively square shape for the diaphragm 20 (FIG. 1d). Aluminum contacts 19 or electrodes 19 were formed on top of the diaphragm 20 using an electron beam evaporator (FIG. 1e). The aluminum contacts 19 or electrodes 19 were then patterned using lift-off.

Nickel-iron (Ni—Fe) Deposition Monitoring

Figure 2:
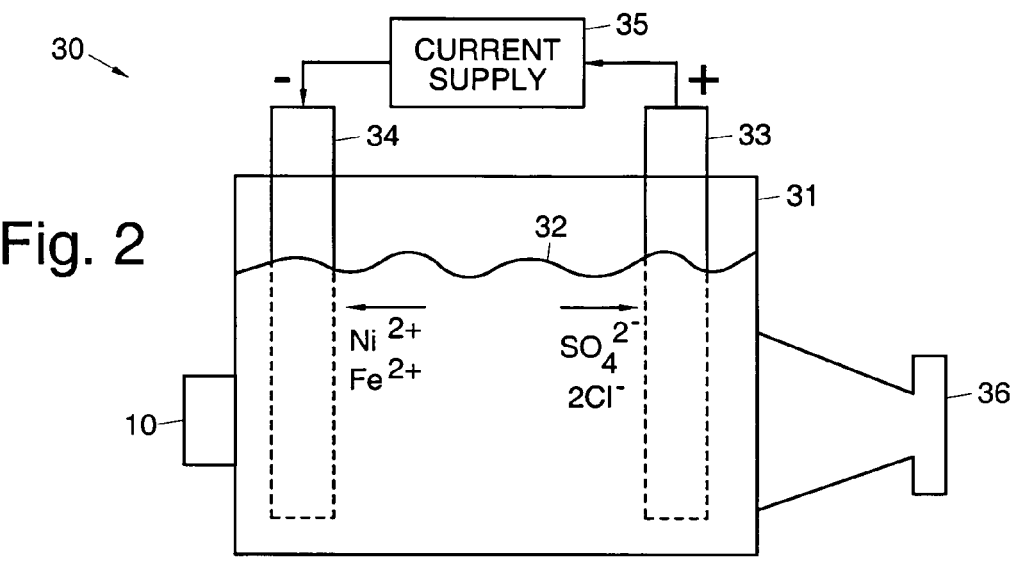
FIG. 2 illustrates in-situ monitoring of an electroplating bath using an exemplary micromachined acoustic sensor.

As is shown in FIG. 2, an electroplating bath 31 was set up using a nickel-iron electroplating solution 32. A nickel anode 33 (positive anode) and a sample cathode 34 (negative cathode) to be plated were placed in the electroplating solution 32. A current supply 35, was interconnected between the nickel anode 33 and the sample cathode 34. A loudspeaker 36 was disposed adjacent the electroplating bath 31 and a prototype reduced to practice sensor 10 was disposed opposite the loudspeaker 36 adjacent the electroplating bath 31.

The variation of acoustic velocity with molarity was first verified experimentally using a commercial piezoelectric sensor. A reduced-to-practice prototype acoustic sensor 10 was then incorporated into a nickel-iron electroplating bath 31 to provide in-situ monitoring of the deposition process (FIG. 2). Theory found in available literature indicates that changes that occur in the solution 32 in the plating bath 31 alter the behavior of a sound wave propagating through the solution 32.

The loudspeaker 36 was used to launch a sound wave through the bath 31 during deposition runs. The sensor 10 was used to monitor pressure changes and indirectly, the changes in the electroplating bath 31. The output of the sensor 10 and the time of the plating deposition were used to predict the Ni—Fe thickness, which was measured after each deposition run.

Figure 3:
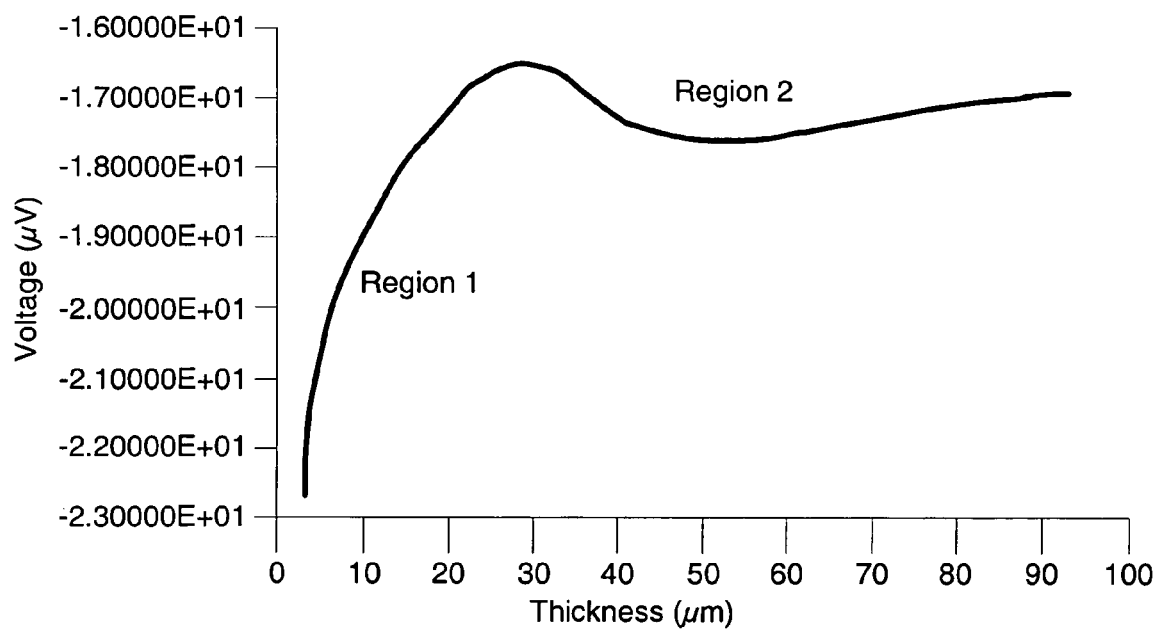
FIG. 3 is a graph that illustrates the output of an exemplary micromachined acoustic sensor versus thickness of an electroplated nickel-iron (Ni—Fe) layer.

A graph showing the output signal from the sensor 10, recorded as a function of total plated thickness, is shown in FIG. 3, which illustrates that the greater the thickness of the Ni—Fe electrodeposit, the smaller the magnitude of the recorded sensor response. Thus, the pressure in the bath 31 decreases with increasing plated thickness as a consequence of ions being plated out of the solution. FIG. 3 displays a greater positive slope in Region 1 than in Region 2 of the graph. Region 1 includes the time period starting with the onset of deposition and during conditioning of the bath. The explanation for this difference between regions is that initially ions deplete out of the system faster or non-uniformly until some stable condition is met resulting in the smaller slope in Region 2. Statistical analysis was used to map the output of the sensor 10 and the plating time to the Ni—Fe thickness. A regression model was generated that provided a good fit to the experimental data. This model derived an equation of metal thickness as a function of the output of the sensor 10 and plating time. The predictive model may be used to provide real-time monitoring of Ni—Fe electroplating, for example.

Thus, a micromachined acoustic sensor for monitoring electrochemical deposition and fabrication methods have been disclosed. It is to be understood that the above-described embodiments are merely illustrative of some of the many specific embodiments that represent applications of the principles of the present invention. Clearly, numerous and other arrangements can be readily devised by those skilled in the art without departing from the scope of the invention.

What is claimed is:

1. A method of monitoring an electrochemical deposition process, comprising:

configuring an electroplating bath comprising electroplating solution, a positive anode disposed in the solution, a negative cathode comprising a sample to be plated disposed in the solution, a current supply interconnected between the anode and the cathode;

disposing a loudspeaker adjacent the electroplating bath;

disposing an acoustic sensor opposite the loudspeaker adjacent the electroplating bath, which sensor comprises a deformable silicon membrane, an encapsulated piezoelectric layer formed on the silicon membrane, and two or more surface electrodes formed on the encapsulated piezoelectric layer;

transmitting an acoustic signal through the electroplating bath for reception by the acoustic sensor while electroplating the sample;

monitoring the acoustic response of the sensor with respect to plating thickness during electroplating of the sample to generate a predictive model defining the plating thickness versus time; and using the predictive model to monitor the plating thickness of samples in real time.

2. The method recited in claim 1 wherein the membrane of the acoustic sensor comprises a doped silicon layer.

3. The method recited in claim 1 wherein the piezoelectric layer comprises zinc oxide.

4. The method recited in claim 1 wherein the piezoelectric layer is encapsulated by a silicon nitride layer.

5. Acoustic sensor apparatus, comprising:

a deformable silicon membrane;

an encapsulated piezoelectric layer directly formed on the silicon membrane; and two or more surface electrodes formed on the encapsulated piezoelectric layer.

6. The apparatus recited in claim 5 wherein the membrane comprises a doped silicon layer.

7. The apparatus recited in claim 5 wherein the piezoelectric layer comprises zinc oxide.

8. The apparatus recited in claim 5 wherein the piezoelectric layer is encapsulated by a silicon nitride layer.

* * * * *

UNITED STATES PATENT AND TRADEMARK OFFICE
CERTIFICATE OF CORRECTION

PATENT NO. : 7,784,346 B2 Page 1 of 1
APPLICATION NO. : 11/199102
DATED : August 31, 2010
INVENTOR(S) : Frances R. Williams and Gary S. May It is certified that error appears in the above-identified patent and that said Letters Patent is hereby corrected as shown below:

The Title of the patent should read as "Micromachined Acoustic Sensor For Monitoring Electrochemical Deposition".

Signed and Sealed this

Sixteenth Day of November, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,784,346 B2 | Page 1 of 1 |
| APPLICATION NO. | : 11/199102 | |
| DATED | : August 31, 2010 | |
| INVENTOR(S) | : Frances R. Williams and Gary S. May | |

It is certified that error appears in the above-identified patent and that said Letters Patent is hereby corrected as shown below:

Title Page, Item (54) and at Column 1, lines 1-3,
The Title of the patent should read as "Micromachined Acoustic Sensor For Monitoring Electrochemical Deposition".

This certificate supersedes the Certificate of Correction issued November 16, 2010.

Signed and Sealed this
Twelfth Day of April, 2011

David J. Kappos
*Director of the United States Patent and Trademark Office*